United States Patent
Badding et al.

(10) Patent No.: US 9,502,729 B2
(45) Date of Patent: Nov. 22, 2016

(54) ION-CONDUCTING COMPOSITE ELECTROLYTE COMPRISING PATH-ENGINEERED PARTICLES

(75) Inventors: Michael Edward Badding, Campbell, NY (US); Jacqueline Leslie Brown, Lindley, NY (US); Katherine A. Fink, Campbell, NY (US); Atanas Valentinov Gagov, Mountain View, CA (US); Cameron Wayne Tanner, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 720 days.

(21) Appl. No.: 13/597,871

(22) Filed: Aug. 29, 2012

(65) Prior Publication Data
US 2014/0065513 A1   Mar. 6, 2014

(51) Int. Cl.
*H01M 8/10* (2006.01)
*G01N 27/40* (2006.01)
*C25B 13/08* (2006.01)
(Continued)

(52) U.S. Cl.
CPC .............. *H01M 8/1058* (2013.01); *C08J 5/22* (2013.01); *C25B 13/04* (2013.01); *C25B 13/08* (2013.01); *G01N 27/40* (2013.01); *H01G 11/56* (2013.01); *H01M 2/166* (2013.01); *H01M 2/1646* (2013.01); *H01M 6/18* (2013.01); *H01M 6/36* (2013.01); *H01M 8/1048* (2013.01); *H01M 10/056* (2013.01); *H01M 10/0525* (2013.01); *H01M 10/0562* (2013.01); *H01M 2300/0091* (2013.01); *Y02E 60/122* (2013.01); *Y02E 60/13* (2013.01); *Y02E 60/521* (2013.01)

(58) Field of Classification Search
None
See application file for complete search history.

(56) References Cited

U.S. PATENT DOCUMENTS

| 3,502,493 A | 3/1970 | Forestek |
| 3,615,841 A | 10/1971 | Smith et al. |

(Continued)

FOREIGN PATENT DOCUMENTS

| EP | 0948074 | 10/1999 |
| EP | 0977296 | 2/2000 |
| EP | 1615286 | 1/2006 |

OTHER PUBLICATIONS

PCT/US13/055943, filed Aug. 21, 2013, PCT Search Report dated Nov. 25, 2013.

(Continued)

*Primary Examiner* — Barbara Gilliam
*Assistant Examiner* — Adam A Arciero
(74) *Attorney, Agent, or Firm* — John L. Haack; Michael W. Russell

(57) ABSTRACT

An ion-conducting composite electrolyte is provided comprising path-engineered ion-conducting ceramic electrolyte particles and a solid polymeric matrix. The path-engineered particles are characterized by an anisotropic crystalline structure and the ionic conductivity of the crystalline structure in a preferred conductivity direction H associated with one of the crystal planes of the path-engineered particle is larger than the ionic conductivity of the crystalline structure in a reduced conductivity direction L associated with another of the crystal planes of the path-engineered particle. The path-engineered particles are sized and positioned in the polymeric matrix such that a majority of the path-engineered particles breach both of the opposite major faces of the matrix body and are oriented in the polymeric matrix such that the preferred conductivity direction H is more closely aligned with a minimum path length spanning a thickness of the matrix body than is the reduced conductivity direction L.

22 Claims, 2 Drawing Sheets

(51) Int. Cl.
*H01M 10/0562* (2010.01)
*H01M 6/36* (2006.01)
*C08J 5/22* (2006.01)
*H01M 2/16* (2006.01)
*H01M 10/0525* (2010.01)
*H01M 10/056* (2010.01)
*H01M 6/18* (2006.01)
*C25B 13/04* (2006.01)
*H01G 11/56* (2013.01)

(56) References Cited

U.S. PATENT DOCUMENTS

| | | | |
|---|---|---|---|
| 3,796,782 | A | 3/1974 | Velde |
| 4,183,988 | A | 1/1980 | Farrington et al. |
| 4,247,499 | A | 1/1981 | Glugla et al. |
| 4,977,007 | A | 12/1990 | Kondo et al. |
| 5,491,039 | A | 2/1996 | Shackle |
| 6,200,707 | B1 | 3/2001 | Takada et al. ............... 429/304 |
| 6,372,387 | B1 | 4/2002 | Kawakami et al. .......... 429/303 |
| 7,820,022 | B2 | 10/2010 | McNulty et al. |
| 2006/0004112 | A1 | 1/2006 | Shimoyama et al. ......... 521/27 |
| 2008/0299462 | A1* | 12/2008 | Whear et al. ................. 429/247 |
| 2009/0136830 | A1* | 5/2009 | Gordon ........................... 429/50 |
| 2010/0015494 | A1* | 1/2010 | Yates et al. ..................... 429/33 |
| 2012/0308872 | A1* | 12/2012 | Huang ........................... 429/149 |
| 2013/0052509 | A1* | 2/2013 | Halalay ................. H01M 2/145 429/129 |

OTHER PUBLICATIONS

Golodnitsky, D. et al.; Ion-transport phenomena in concentrated PEO-based composite polymer electrolytes; Solid State Ionics; vol. 147, pp. 141-155; 2002.

Radziuk, D. et al.; Spectroscopic Investigation of Composite Polymeric and Monocrystalline Systems with Ionic Conductivity; Polymers, vol. 3, pp. 674-692, 2011.

Te Velde, T.S. et al.; Monograin layers; Philips Technical Review; vol. 29, pp. 238-242, 1968.

Adachi, G. et al.; Fast Li Conducting Ceramic Electrolytes; Advanced Materials; vol. 8, Issue 2, pp. 127-135; 1996.

Skaarup, S. et al.; Mixed phase solid electrolytes; Solid State Ionics; vol. 28-30; Part 2, pp. 975-978; 1988.

Skaarup, S. et al.; Mixed phase solid electrolytes with nonconducting polymer binder; Solid State Ionics; vol. 40-41, pp. 1021-1024; 1990.

Plocharski, J. et al.; PEO based composite solid electrolyte containing nasicon; Solid State Ionics; vol. 28-30, pp. 979-982; 1988.

MacFarlane, D. et al.; Lithium-ion conducting ceramic/polyether composites; Electrochimica acta; vol. 43, No. 10-11, pp. 1333-1337; 1998.

Nairn K. et al.; Ceramic-polymer interface in composite electrolytes of lithium aluminium titanium phosphate and polyetherurethane polymer electrolyte; Solid State Ionics; vol. 121, No. 1-4, pp. 115-119; 1999.

Cretin, M. et al.; Comparative study of lithium ion conductors in the system $Li1+xAlxA2-xIV (PO4)3$ with $AIV=Ti$ or Ge and $0 \leq x \leq 0-7$ for use as Li sensitive membranes; Journal of the European Ceramic Society; vol. 19, Issue 16, pp. 2931-2940; 1999.

Cretin, M. et al; Nasicon structure for alkaline ion recognition; Sensors and Actuators B: Chemical; vol. 43, Issues 1-3, pp. 224-229; 1997.

Kingery et al.; Introduction to Ceramics; Second Edition; 1976; pp. 475-478; John Wiley & Sons; New York, NY; ISBN 0-471-47860-1-book.

International Search Report, issued in connection with corresponding PCT application No. PCT/US13/055943, Nov. 25, 2013.

\* cited by examiner

ION-CONDUCTING COMPOSITE ELECTROLYTE COMPRISING PATH-ENGINEERED PARTICLES

BACKGROUND

Field

The present disclosure relates to ion-conducting electrolytes and assemblies incorporating ion-conducting electrolytes.

Technical Background

Ion-conducting electrolytes have been proposed for use in a wide variety of technological applications including lithium ion batteries, sodium sulfur batteries, solid oxide fuel cells, oxygen separators, electrolyzers, sensors, chemical reactors, etc.

BRIEF SUMMARY

The present inventors have recognized significant unrealized potential in ion-conducting ceramic electrolytes and attribute this unrealized potential to a general tendency to turn to polycrystalline ceramic electrolytes, which are often more practical to manufacture than single crystal ceramic electrolytes. However, grain boundaries in polycrystalline ceramic electrolytes limit the ionic conductivity of the electrolyte. Additionally, polycrystalline ceramic electrolytes often exhibit poor mechanical properties and are often difficult to manufacture and incorporate into electrochemical devices. Ion-conducting composite electrolytes according to the subject matter of the present disclosure comprise path-engineered ion-conducting ceramic electrolyte particles positioned in a solid polymeric matrix and can be configured to confer flexibility and strain tolerance that exceeds that which is possible with a conventional ceramic electrolytes.

In accordance with various embodiments of the present disclosure, an ion-conducting composite electrolyte is provided comprising path-engineered ion-conducting ceramic electrolyte particles and a solid polymeric matrix. The path-engineered particles are characterized by an anisotropic crystalline microstructure where the ionic conductivity of the crystalline structure in a preferred conductivity direction H associated with one of the crystal planes of the path-engineered particle is larger than the ionic conductivity of the crystalline structure in a reduced conductivity direction L associated with another of the crystal planes of the path-engineered particle. The path-engineered particles are sized and positioned in the polymeric matrix such that a majority of the path-engineered particles breach both of the opposite major faces of the matrix body and are oriented in the polymeric matrix such that the preferred conductivity direction H is more closely aligned with a minimum path length spanning a thickness of the matrix body than is the reduced conductivity direction L.

In accordance with other embodiments of the present disclosure, an ion-conducting composite electrolyte is provided where the path-engineered particles are characterized by an isotropic crystalline structure.

In accordance with still further embodiments of the present disclosure, methods of preparing ion-conducting composite electrolytes involve preparing path-engineered particles for inclusion in a polymeric matrix by subjecting ceramic precursor crystals to thermally-induced microcracking. The micro-cracked precursor crystals can be separated into individual path-engineered ion-conducting ceramic electrolyte particles.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1A:
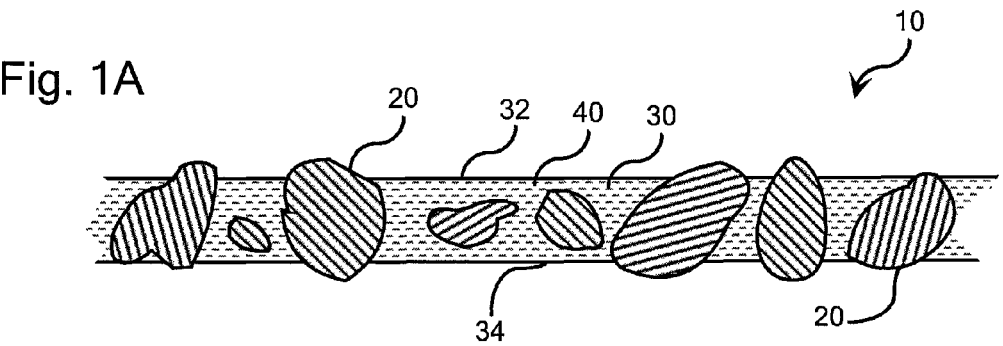
FIG. 1A is a schematic illustration of a portion of one type of ion-conducting composite electrolyte according to the present disclosure.

Referring initially to FIG. 1A, a portion of an ion-conducting composite electrolyte 10 is illustrated schematically and comprises path-engineered ion-conducting ceramic electrolyte particles 20, a solid polymeric matrix 30, and, optionally, a fiber stiffener component 40 distributed throughout the polymeric matrix 30. The respective shapes of the path-engineered particles 20 may vary significantly from particle to particle and is not illustrated with particular precision in FIG. 1A. Rather, the path-engineered particles 20 of FIG. 1A are merely presented to show their presence in the polymeric matrix 30 and to show that their size and shape will typically vary across the composite electrolyte 30. Similarly, the size and shape of the path-engineered particles illustrated in FIGS. 1B and 1C, described in further detail below, have been intentionally simplified for illustrative purposes.

As is illustrated in FIG. 1A, the polymeric matrix defines a pair of opposite major faces 32, 34 defining a matrix body there between. The path-engineered particles 20 are sized and positioned in the polymeric matrix 30 such that a majority of the path-engineered particles 20 breach, i.e., are flush with or extend beyond, both of the opposite major faces 32, 34 of the matrix body. It is contemplated that the path-engineered particles may be advantageously characterized by an anisotropic crystalline structure, although isotropic crystalline structures are also contemplated.

Figure 1C:
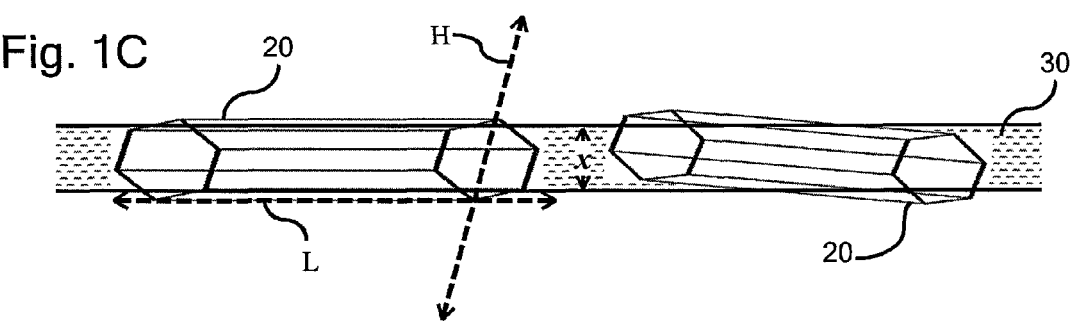
FIGS. 1B and 1C present schematic illustrations of some of the many ways in which path engineered particles can be oriented in an ion-conducting composite electrolyte according to the present disclosure.
Figure 1B:
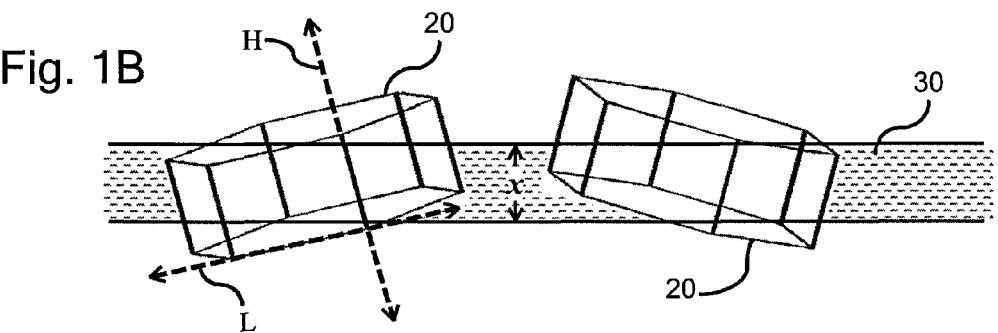

Referring for example to the hexagonal crystalline structures illustrated in FIGS. 1B and 1C, it is contemplated that the path-engineered particles 20 can be selected such that they are characterized by an anisotropic crystalline structure. In which case, the particles can be selected such that the ionic conductivity of the crystalline structure in a preferred conductivity direction H associated with one of the crystal planes of the path-engineered particle 20 is larger than the ionic conductivity of the crystalline structure in a reduced conductivity direction L associated with a different crystal plane of the path-engineered particle 20. In this manner, substantially all, or at least a majority of, the path engineered particles 20 can be oriented in the polymeric matrix 30 such that the preferred conductivity direction H is more closely aligned with a minimum path length x spanning a thickness of the matrix body, i.e., more closely aligned than the reduced conductivity direction L. This alignment is illustrated schematically in FIGS. 1B and 1C and can lead to a composite electrolyte with enhanced ionic conductivity, typically on the order of approximately $10^{-4}$ S/cm or greater. For example, and not by way of limitation, in the context of lithium-aluminum titanium phosphate (LATP) path-engineered particles 20, the ionic conductivity of the crystalline structure in the preferred conductivity direction H is approximately one order of magnitude larger than the ionic conductivity of the crystalline structure in the reduced conductivity direction L.

To encourage the aforementioned orientation, it is contemplated that the path engineered particles 20 can be sized such that a size dimension of the path-engineered particle 20 in the preferred conductivity direction H is smaller than a size dimension of the path-engineered particle 20 in the reduced conductivity direction L. The difference in the respective size dimensions of the path-engineered particle 20 can be used to encourage self-alignment of the path engineered particles in the aforementioned orientation because, in many of the contemplated fabrication processes described herein a particle will naturally tend to settle in an orientation that is strongly influenced by the relative size dimensions of the particle in different directions.

For path-engineered particles characterized by an isotropic crystalline structure, the aforementioned selective orientation would not typically be necessary. Examples of suitable isotropic crystalline structures include, but are not limited to, lithium ion conductors with the cubic garnet structure such as aluminum-stabilized $Li_7La_3Zr_2O_{12}$, or with the perovskite structure such as $Li_{3x}La_{0.67-x}TiO_3$, and typically lead to a composite electrolyte with enhanced ionic conductivity typically on the order of approximately $1 \times 10^{-4}$ S/cm or greater.

Particular embodiments of the present disclosure relate to the advantageous use of path-engineered particles 20 that are characterized by hexagonal crystalline structures. More specifically, referring to FIG. 1B, in the context of path-engineered particles 20 comprising hexagonal crystalline structures, the present inventors have recognized that the ionic conductivity of the composite electrolyte 10 can be enhanced by ensuring that a majority, or substantially all, of the path engineered particles 20 are oriented in the polymeric matrix 30 such that the minimum path length x spanning a thickness of the matrix body is more closely aligned with the relatively high conductivity crystallographic direction H than with the relatively low conductivity crystallographic direction L.

Regarding contemplated compositions of path-engineered particles 20 according to the present disclosure, in particular embodiments, the path-engineered particles 20 will comprise an ion-conducting ceramic, such as, for example, a lithium ion-conducting ceramic like LATP or a derivative thereof. Such materials may possess internal inclusions that typically comprise aluminum phosphate, titanium dioxide, aluminum oxide, or combinations thereof. Additional contemplated embodiments will include path engineered particles comprising an ion-conducting ceramic selected from lithium metal phosphates, sodium zirconia phosphates, sodium beta aluminate, fluorites, and ceramic oxides with garnet-type crystalline structures. The composition or choice of material is selected partly based upon the ability to grow crystals by a convenient technique like the Czochralski process. Examples of such materials are $LiNbO_3$, $YVO_4$, $Al_2O_3$, and $Ce_2O_3$-doped $Y_3Al_5O_{12}$ (YAG:Ce). It is noted that the compositional profile of contemplated composite electrolytes can be controlled by doping to attain desired properties.

Figure 2:
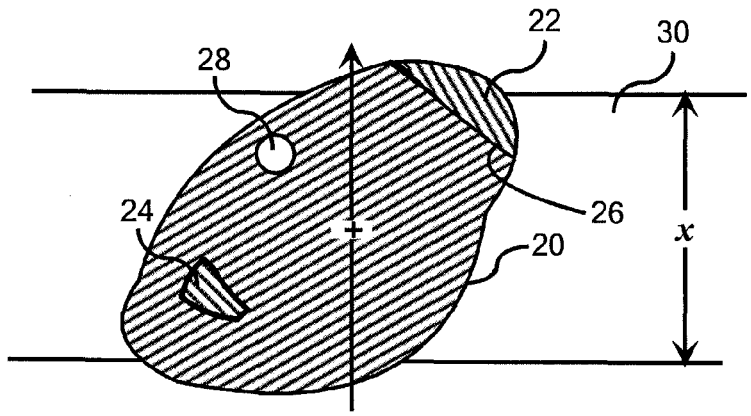
FIG. 2 is a detailed schematic illustration of a path-engineered particle for use in ion-conducting composite electrolytes according to the present disclosure.
Figure 3:
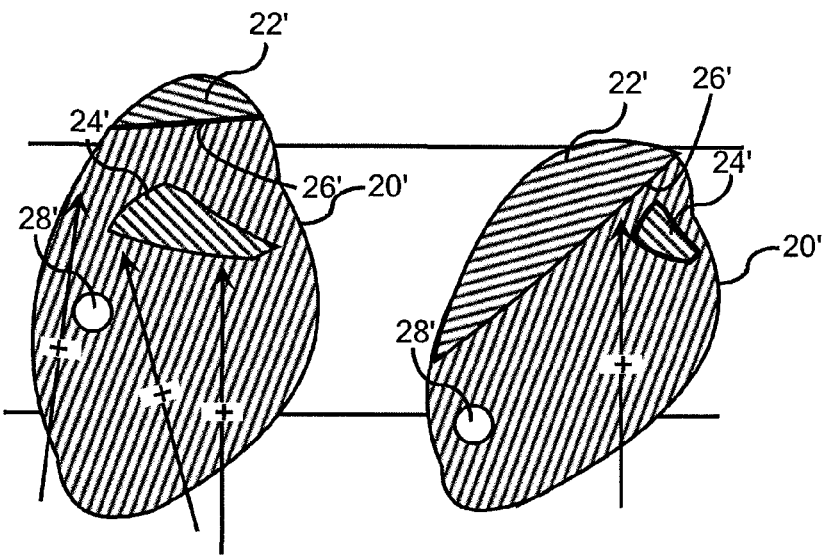
FIG. 3 illustrates particles comprising impeded linear ion-conducting paths.

As is illustrated in FIG. 2, it is contemplated that a majority of the face-breaching, path-engineered particles 20 may comprise internal inclusions in the form of primary inclusions 22 and secondary phase inclusions 24, grain boundaries 26, pores 28, or combinations thereof. In this context, the path-engineered particles 20 can be oriented in the polymeric matrix 30 to comprise a breaching cross section, examples of which are illustrated schematically in FIGS. 1 and 2. The breaching cross section defines a cross-body, linear ion-conducting path (+) that is unimpeded by the internal inclusions 22, 24, the grain boundaries 26, and the pores 28 of the particle 20. To clarify, by contrast, the linear ion-conducting paths (+) of the particles 20' illustrated in FIG. 3 are impeded by the internal inclusions 22', 24', the grain boundaries 26' and the pores 28', and as such are not cross-body, linear ion-conducting paths. By incorporating the aforementioned cross-body, linear ion-conducting path composite electrolytes according to the present disclosure eliminate, or substantially reduce, the impact of grain boundaries on ionic transport.

As is illustrated in the example of FIG. 2, it is contemplated that a face-breaching, path-engineered particle 20 according to the present disclosure may comprise a single crystal majority, by volume, that is free of grain boundaries, although a remaining volume of the particle itself comprises a minority of grain boundaries 26, internal inclusions 22, 24 and pores 28. Typically, the remaining volume comprises primary phase inclusions of distinct crystal orientation, secondary phase inclusions, pores, or combinations thereof and occupies between approximately 0.1% and approximately 20%, by volume, of the face-breaching, path-engineered particle 20.

It is also contemplated that the aforementioned unimpeded linear ion-conducting paths (+) may be more readily achieved by ensuring that the grain boundaries 26 of the path engineered particles 20 span less than a majority of the breaching cross section of the face-breaching, path-engineered particles in a direction substantially parallel to the major faces of the matrix body. An example of a grain boundary satisfying this condition is illustrated in FIG. 2, while the right-hand side particle 20' illustrated in FIG. 3 includes a grain boundary 26' that does not satisfy this condition.

As is further illustrated in FIG. 2, preferably, at least a majority of the path-engineered particles 20 are oriented in the polymeric matrix 30 such that respective breaching cross sections of the particles 20 define a cross-body, linear ion-conducting path that is unimpeded by the secondary phase inclusions 24, grain boundaries 26, and closed pores 28 of the face-breaching, path-engineered particle 20.

Regarding the volumetric composition of the composite electrolyte 10, it is contemplated that particular embodiments will comprise (i) between approximately 10% and approximately 95% of the face-breaching, path-engineered particles 20 (ii) between approximately 5% and approximately 90% of the polymeric matrix 30, and (iii) between approximately 0.1% and approximately 20% of impeded-path ion-conducting ceramic electrolyte particles 20', by volume. For the purposes of defining and describing aspect of the present disclosure, it is noted that impeded-path ion-conducting particles 20' are particles that do not comprise the above-described unimpeded cross-body, linear ion-conducting path, either because they are dominated by inclusions 24', grain boundaries 26', and/or pores 28', are primarily polycrystalline, or do not breach both of the opposite major faces of the matrix body. More preferably, it is contemplated that, in some embodiments, the composite electrolyte 10 comprises at least approximately 20% of the face-breaching, path-engineered particles 20, by volume.

Regarding the dimensional characteristics of the composite electrolyte 10, it is contemplated that, in particular embodiments, the path-engineered particles will define an average size ($d_{50}$) of between approximately 10 µm and approximately 1 mm with a size dispersion (($d_{90}-d_{10}$)/$d_{50}$) that is less than approximately 1.0. It is also contemplated that the composite electrolyte 10 will often advantageously define a thickness of between approximately 10 µm and approximately 50 µm. It is contemplated that the thickness of a composite electrolyte according to the present disclosure for any given application is a function of its conductivity, mechanical strength, and methods of preparation. It may range from a few microns up to about 1 mm. Within a given composite electrolyte membrane, a narrow dispersion in the size of the path engineered particles 20 is preferred. Grains that are too large would protrude far above the surface of the polymer and would potentially interfere with sheet forming processes, assembly, and the like. Particles that are smaller than the thickness of the polymer cannot span the membrane and provide a conductive pathway.

Crystalline structures used for the composite electrolytes of the present disclosure need not be regular in shape nor compositionally uniform or free of inclusions. Crystals of the type required for the composite electrolyte can be prepared efficiently by techniques such as prolonged sintering to allow grain growth or by slow cooling from the melt. The product of either process can then be ground and selectively sized by sieving, air-classification, etc.

Methods of preparing ion-conducting composite electrolytes 10 according to the present disclosure involve preparing the path-engineered particles 20 for inclusion in the polymeric matrix 30 by subjecting ceramic precursor crystals to thermally-induced microcracking. The microcracked precursor crystals can subsequently be separated into individual path-engineered ion-conducting ceramic electrolyte particles 20. The composite electrolyte 10 including the path-engineered particles 20 and the polymeric matrix 30 may be assembled by a variety of suitable techniques including, without limitation, injection molding, compression molding, roll molding, film casting, spin coating alone on in conjunction post forming techniques like plasma etching, mechanical abrasion, laser ablation to expose the particles and enable ionic conduction. In some embodiments, contemplated composite electrolyte membranes can be formed by polymer processing techniques without sintering.

For example, and not by way of limitation, relatively large crystals of lithium ion-conducting LATP ($Li_{1.3}Al_{0.3}Ti_{1.7}(PO_4)_3$) were prepared by extending sintering. The reactants for the two batches listed in the table below were dry blended in a total amount of about 2 kg each, transferred into platinum crucibles, reacted for 12 hours at 190° C., reacted 12 hours and 800° C. to partially form the LATP crystalline structure, and then vibratory milled.

|  | Weight Percent | |
| --- | --- | --- |
| Batch Material | 625 EQP | 625 EQM |
| L22 - $Li_2CO_3$ | 11.656 | — |
| L510 - $LiH_2PO_4$ | — | 33.205 |
| A121 - $Al(PO_3)_3$ | 19.213 | 19.457 |
| T26 - $TiO_2$ | 32.962 | 33.383 |
| P4 - $P_2O_5$ | 36.169 | 13.955 |

The milled powder was formed into ~25 mm diameter pills by uniaxially pressing. The pills were sintered at temperatures and times listed in Table #2 to induce grain growth.

| | Weight Percent of Phase | | | Microtrac PSD (µm) | | | |
| --- | --- | --- | --- | --- | --- | --- | --- |
| Sample/Temp/Time | $LiTi_2(PO_4)_3$ | $TiO_2$ (Rutile) | $AlPO_4$ | d10 | d50 | d90 | ($d_{90} - d_{10}$) $d_{50}$ |
| EQM 1150° C. 100 hrs | 97 | 1.5 | 2 | 185 | 359 | 530 | 0.96 |
| EQM 1150° C. 150 hrs | 89 | 5.2 | 6.3 | 74 | 288 | 481 | 1.41 |
| EQM 1150° C. 240 hrs | 93 | 1.6 | 5.4 | 165 | 355 | 535 | 1.04 |
| EQP 1150° C. 100 hrs | 98 | 0.7 | 0.8 | 126 | 303 | 466 | 1.12 |
| EQP 1150° C. 150 hrs | 94 | 2.9 | 3 | 38 | 89 | 257 | 2.47 |
| EQP 1150° C. 240 hrs | 96 | 0.6 | 3.5 | 44 | 102 | 373 | 3.23 |
| S-70 Steel Shot | | | | 253 | 318 | 410 | 0.49 |

The resulting grains are roughly equiaxed and have size determined visually from 300 to more than 1000 µm.

The grains in the pills were further processed into a powder that is made of particles that are themselves predominantly single crystals. Although it is possible to imagine grinding, jet milling or another high energy technique to separate the particles and reduce their sizes, this was not necessary with LATP. The crystalline structure of LATP is not cubic, and is subject to microcracking as a result of its large thermal expansion anisotropy. The critical grain size for microcracking is estimated to be about 0.5 µm. This critical grain size is almost two orders of magnitude smaller than those obtained by extended sintering. The pills were extensively microcracked and with only the mildest of forces crumbled into individual crystals.

It is contemplated that relatively large crystals can be achieved through nucleation and growth from a melt. In one example, LATP crystals were grown starting with the reactants listed in the following table:

| Batch Material | 625 EQT $Li_{1.15}Al_{0.15}Ti_{1.85}(PO_4)_3$ | 625 EQU $Li_{1.3}Al_{0.3}Ti_{1.7}(PO_4)_3$ | 625 EQV $Li_{1.4}Al_{0.4}Ti_{1.6}(PO_4)_3$ |
|---|---|---|---|
| L510 - $LiH_2PO_4$ | 29.418 | 33.205 | 35.724 |
| A121 - $Al(PO_3)_3$ | 9.743 | 19.458 | 25.918 |
| T26 - $TiO_2$ | 36.382 | 33.383 | 31.388 |
| P4 - $P_2O_6$ | 24.457 | 13.954 | 6.970 |

The resulting raw materials were dry blended, transferred into a platinum crucible, heated at ~100° C./hr to 1600° C., and then cooled at a rate of 10° C./hr to 100° C. The morphology of the product in the crucibles showed that crystals with size well above 1 mm were obtained by this technique. One would not necessarily predict that an off-stoichiometry composition would crystallize to give a nearly single phase product. For this reason, it is contemplated that the methodology may be applied to LATP or other ionically conducting materials that are disposed for use in a composite electrolyte.

In one embodiment, spin-coating and chemical etching were applied to produce a composite electrolyte membrane by starting with 4 g of a 5:1 PDMS solution, 1 g of 625 EQU ground and sieved to give particles with sizes ranging from 250-355 µm, spin coating at 500 rpm for 10 seconds, and lastly etching both surfaces in a batch of NMB/TBAF for 15 minutes to remove residual silicone. The thickness of the silicone in the as-finished membrane, i.e. between the LATP particles, was about 140 µm, which is significantly thinner than the lithium ion-conducting crystal particles. For a specimen with an active area of 72.4 mm², the DC resistance of the membrane was taken as approximately 175Ω. With geometric factors of the electrolyte membrane taken into account, this translates to a lithium ion conductivity of $2.7 \times 10^{-4}$ S/cm, more than four-fold greater than the highest value reported for a polycrystalline sample of the same composition.

For many forming techniques, a residual overcoat of polymer on the surface of the conducting particles will be an inherent result of the process. This residual is likely to block movement of the mobile ion that the electrolyte carries and degrade conductivity. The residual can be removed by a variety of techniques, including, but not limited to, chemical etching, polishing, mechanical abrasion, refractive ion etching, ozone plasma treatment, and laser ablation.

Figure 4:
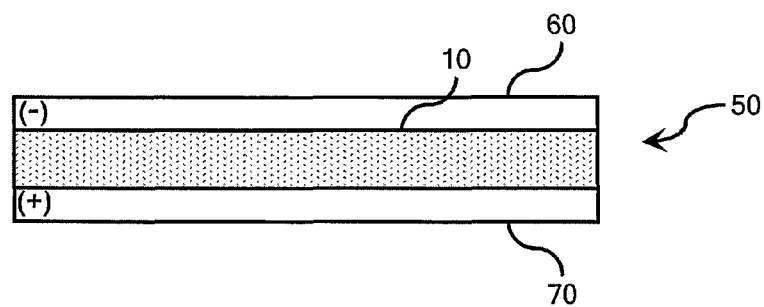
FIG. 4 illustrates an electrochemical device comprising a cathode and an anode separated by a composite electrolyte.

Referring to FIG. 4, it is noted that composite electrolytes 10 according to the present disclosure provide several parameters that may be adjusted and tailored to improve the performance of electrochemical devices 50 incorporating the electrolyte 10. Contemplated parameters include, but are not limited to average particle size, the dispersion in their size, the conductivity of single crystal components of the particles, their orientation, the thickness of the polymer membrane, and the degree of exposure of the particles beyond the major faces of the polymeric matrix in which they are positioned. These and other parameters may be selected to improve electrochemical performance attributes such as power density or response speed and/or mechanical performance attributes that facilitate handling, in-service durability, or device lifetime.

From an electrochemical perspective, the primary benefits created by a composite electrolyte are a higher ionic conductivity and equivalent or lower area specific resistance (ASR) than what can be achieved in an optimized polycrystalline membrane that conducts the same ionic species. For example, the ionic conductivity within a crystal of doped polycrystalline lithium titanium phosphate and lithium germanium phosphate ceramics is a factor of 50 to 100 times greater than realized in the polycrystalline state as a whole. On average, the single crystal conductivity of these doped titanium and germanium phosphates approaches or exceeds $10^{-3}$ S/cm.

Figure 5:
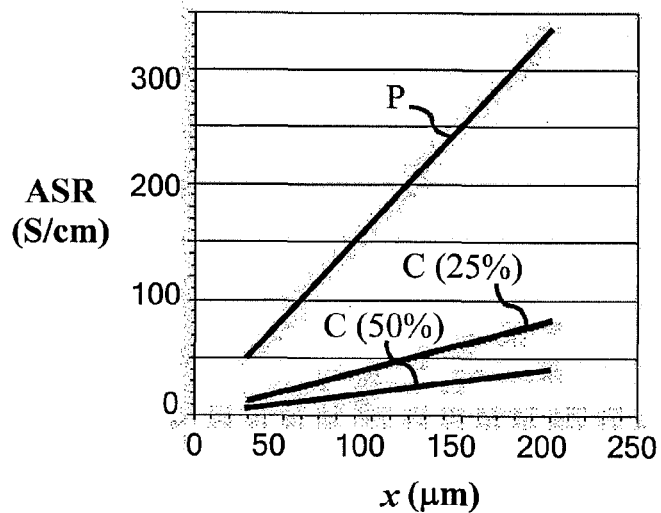
FIG. 5 is a plot of area specific resistance versus membrane thickness.

Referring to FIG. 5, it is noted that ASR is a key figure of merit used to judge the power generating capability of an electrochemical device or its components, i.e., its electrolyte membrane. The ASR of the electrolyte is the dominant contributor to the total ASR of a device if its conductivity is low and the membrane thickness is large. In FIG. 5, the ASR of a composite electrolyte C based upon single crystals of the composition $Li_{1.3}Al_{0.3}Ti_{1.7}(PO_3)_3$ is compared to a sintered polycrystalline electrolyte P of the same composition as a function of membrane thickness x. The figure illustrates two solids loadings, 25% and 50%, of single crystals in the composite electrolyte. It also assumes that the single crystals are flush with the polymer surface, that is to say they do not bulge from the surface of the electrolyte. It is also assumed that the surfaces of the single crystals are fully exposed, i.e. no polymer overcoat, and that the crystals have a uniform cross-section and are oriented normal to the plane of the membrane. Under these conditions, the composite electrolyte even with only a 25% volume loading in the membrane provide an ASR that is a factor of four lower than the polycrystalline electrolyte of the same thickness. The advantage grows larger for the composite electrolyte as the volume loading of single crystals is increased to 50%

It is not necessary to utilize the low ASR of the membrane to improve electrochemical performance. It can be traded for other attributes. For example, the ASR of a polycrystalline electrolyte that is thin may be acceptable from and electrochemical standpoint for application in a device. However, its thin nature might make manufacturing difficult or compromise the durability of the device. The composite electrolyte because of its inherently higher conductivity can be made with an equivalent ASR but with a much greater thickness to overcome such issues. Another possibility is to impart a maximum level of flexibility to the membrane. This can be accomplished by minimizing the amount of single crystal ion conductor within the composite. The ASR calculation represented in FIG. 5 provides the basis for both of these possibilities.

It is contemplated that composite electrolytes described herein can be the source of numerous advantages with respect to the start of the art. For example, contemplated composite electrolytes are likely to exhibit ionic conductivity that is greater than that which would be available from comparable polycrystalline ceramic electrolytes. Further, contemplated composite electrolyte structures are likely to be more easily handled during processing and device assembly steps and are less likely to be subject to abrupt or unpredictable mechanical failure. The ionic conductivity of contemplated composite electrolyte structures can be traded for increased mechanical integrity by thickening the electrolyte while still maintaining sufficiently high electrochemical performance.

Although the concepts of the present disclosure are described herein with primary reference to a composite electrolyte structure, it is contemplated that the concepts will enjoy applicability to any device that employs an electrolyte structure. For example, and not by way of limitation, it is contemplated that the concepts of the present disclosure will enjoy applicability to a variety of electrochemical devices including, but not limited to, lithium ion batteries, sodium sulfur batteries, solid oxide fuel cells, oxygen separators, electrolyzers, sensors, chemical reactors, etc. By way of illustration, and not limitation, FIG. 4 illustrates an electrochemical device 50 comprising a cathode 60 and an anode 70 separated by a composite electrolyte 10.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. An ion-conducting composite electrolyte comprising ion-conducting ceramic electrolyte particles and a solid polymeric matrix, wherein:
    the solid polymeric matrix comprises a first major face, a second major face opposing the first major face, a matrix body defined between the first and second major face, and a minimum path length x spanning a thickness of the matrix body;
    the ion-conducting ceramic electrolyte particles are characterized by an anisotropic crystalline structure comprising a plurality of crystal planes;
    each ion-conducting ceramic electrolyte particle of a majority of the ion-conducting ceramic electrolyte particles comprises a first crystal plane and a second crystal plane;
    the first crystal plane extends in a direction H and comprises a first ionic conductivity in the direction H;
    the second crystal plane extends in a direction L different from the direction H and comprises a second ionic conductivity in the direction L;
    the first ionic conductivity in the direction H is larger than the second ionic conductivity in the direction L;
    each ion-conducting ceramic electrolyte particle of the majority of the ion-conducting ceramic electrolyte particles is oriented in the solid polymeric matrix such that the direction H is more closely aligned with the minimum path length x than is the direction L; and
    each ion-conducting ceramic electrolyte particle of the majority of the ion-conducting ceramic electrolyte particles is sized and positioned in the solid polymeric matrix to breach both the first and the second major faces of the solid polymeric matrix.

2. An ion-conducting composite electrolyte as claimed in claim 1 wherein the ionic conductivity of the crystalline structure in the direction H is approximately one order of magnitude larger than the ionic conductivity of the crystalline structure in the direction L.

3. An ion-conducting composite electrolyte as claimed in claim 1 wherein:
    the majority of ion-conducting ceramic electrolyte particles are sized such that a size dimension of the ion-conducting ceramic electrolyte particle in the direction H is smaller than a size dimension of the ion-conducting ceramic electrolyte particle in the direction L; and
    the difference in the respective size dimensions of the ion-conducting ceramic electrolyte particle encourages self-alignment of the ion-conducting ceramic electrolyte particles in the solid polymeric matrix, where the direction H is more closely aligned with the minimum path length x spanning a thickness of the matrix body than is the direction L.

4. An ion-conducting composite electrolyte as claimed in claim 1 wherein:
    the ion-conducting ceramic electrolyte particles are characterized by a hexagonal crystalline structure;
    the ionic conductivity of the hexagonal crystalline structure in the direction H lying in the plane of the crystal is larger than the ionic conductivity of the hexagonal crystalline structure in the direction L normal to the plane of the crystal; and
    a majority of the ion-conducting ceramic electrolyte particles are oriented in the solid polymeric matrix such that the minimum path length x spanning a thickness of the matrix body is more closely aligned with the direction H than with the direction L.

5. An ion-conducting composite electrolyte as claimed in claim 1 wherein:
    the ion-conducting ceramic electrolyte particles are characterized by a hexagonal crystalline structure;
    the ionic conductivity of the hexagonal crystalline structure in the direction H lying in the plane of the crystal is larger than the ionic conductivity of the hexagonal crystalline structure in the direction L normal to the plane of the crystal; and approximately all of the ion-conducting ceramic electrolyte particles are oriented in the polymeric matrix such that a minimum path length x spanning a thickness of the matrix body is more closely aligned with the direction H than with the direction L.

6. An ion-conducting composite electrolyte as claimed in claim 1 wherein a majority of the face-breaching, ion-conducting ceramic electrolyte particles comprise internal inclusions and grain boundaries and are oriented in the solid polymeric matrix to comprise a breaching cross section defining a cross-body, linear ion-conducting path that is unimpeded by one or more secondary phase inclusions and the grain boundaries of the face-breaching, ion-conducting ceramic electrolyte particle.

7. An ion-conducting composite electrolyte as claimed in claim 1 wherein:
respective ones of the face-breaching, ion-conducting ceramic electrolyte particles comprise a single crystal majority, by volume, in each ion-conducting ceramic electrolyte particle;
the single crystal majority is free of grain boundaries; and
a remaining volume of respective ones of the face-breaching, ion-conducting ceramic electrolyte particles comprises primary phase inclusions of distinct crystal orientation, secondary phase inclusions, pores, or combinations thereof.

8. An ion-conducting composite electrolyte as claimed in claim 1 wherein a majority of the face-breaching, ion-conducting ceramic electrolyte particles comprise grain boundaries that span less than a majority of the breaching cross section of the face-breaching, ion-conducting ceramic electrolytes particles in a direction approximately parallel to the major faces of the matrix body.

9. An ion-conducting composite electrolyte as claimed in claim 1 wherein a majority of the face-breaching, ion-conducting ceramic electrolyte particles comprise internal inclusions, grain boundaries, and closed pores and are oriented in the solid polymeric matrix to comprise a breaching cross section defining a cross-body, linear ion-conducting path that is unimpeded by one or more secondary phase inclusions, the grain boundaries, and the closed pores of the face-breaching, ion-conducting ceramic electrolyte particle.

10. An ion-conducting composite electrolyte as claimed in claim 1 wherein the ion-conducting ceramic electrolyte particles comprise an ion-conducting ceramic.

11. An ion-conducting composite electrolyte as claimed in claim 1 wherein the ion-conducting ceramic electrolyte particles comprise a lithium ion-conducting ceramic.

12. An ion-conducting composite electrolyte as claimed in claim 11 wherein the lithium ion-conducting ceramic comprises lithium-aluminum titanium phosphate (LATP) or a derivative thereof.

13. An ion-conducting composite electrolyte as claimed in claim 12 wherein one or more internal inclusions comprise inclusions of aluminum phosphate, titanium dioxide, aluminum oxide, or combinations thereof.

14. An ion-conducting composite electrolyte as claimed in claim 1 wherein the ion-conducting ceramic electrolyte particles comprise an ion-conducting ceramic selected from lithium metal phosphates, sodium zirconia phosphates, sodium beta alumina, fluorites, and ceramic oxides with garnet-type crystalline structures.

15. An ion-conducting composite electrolyte as claimed in claim 1 wherein the ion-conducting ceramic electrolyte particles are sintered.

16. An ion-conducting composite electrolyte as claimed in claim 1 wherein the ion-conducting ceramic electrolyte particles define an average size ($d_{50}$) of between approximately 10 μm and approximately 1 mm with a size dispersion (($d_{90}-d_{10}$)/$d_{50}$) that is less than approximately 1.0.

17. An ion-conducting composite electrolyte as claimed in claim 1 wherein the ion-conducting composite electrolyte is characterized by an ionic conductivity that is on the order of approximately $10^{-4}$ S/cm or greater.

18. An ion-conducting composite electrolyte as claimed in claim 17 wherein the composite electrolyte comprises at least approximately 20% by volume of the majority of the ion-conducting ceramic electrolyte particles.

19. An ion-conducting composite electrolyte as claimed in claim 1 wherein the composite electrolyte defines a thickness of between approximately 10 μm and approximately 50 μm.

20. An ion-conducting composite electrolyte as claimed in claim 1 wherein the composite electrolyte further comprises a fiber stiffener component distributed throughout the solid polymeric matrix.

21. An ion-conducting composite electrolyte as claimed in claim 1 wherein the composite electrolyte is comprised within a lithium ion battery, a sodium sulfur battery, a solid oxide fuel cell, an oxygen separator, a sensor, a dehydrogenating chemical reactor, or a device comprising a cathode and an anode separated by the composite electrolyte.

22. A method of preparing an ion-conducting composite electrolyte comprising ion-conducting ceramic electrolyte particles and a solid polymeric matrix, the method comprises:
preparing the ion-conducting ceramic electrolyte particles for inclusion in the solid polymeric matrix by subjecting ceramic precursor crystals to thermally-induced microcracking; and
separating the microcracked precursor crystals into individual ion-conducting ceramic electrolyte particles, wherein:
the solid polymeric matrix comprises a first major face, a second major face opposing the first major face, a matrix body defined between the first and second major faces;
each ion-conducting ceramic electrolyte particle of the majority of the ion-conducting ceramic electrolyte particles is sized and positioned in the solid polymeric matrix to breach both the first and the second major faces of the solid polymeric matrix;
the ion-conducting ceramic electrolyte particles are characterized by an anisotropic crystalline structure; and
a majority of the face-breaching, ion-conducting ceramic electrolyte particles comprise internal inclusions and grain boundaries and are oriented in the solid polymeric matrix to comprise a breaching cross section defining a cross-body, linear ion-conducting path that is unimpeded by one or more secondary phase inclusions and the grain boundaries of the face-breaching, ion-conducting ceramic electrolyte particle.

* * * * *